(12) United States Patent
Nelson et al.

(10) Patent No.: US 8,178,709 B2
(45) Date of Patent: May 15, 2012

(54) IRON PREPARATION SUITABLE FOR PHARMACEUTICAL FORMULATION AND PROCESS FOR THE PREPARATION THEREOF

(75) Inventors: Deanna Jean Nelson, Raleigh, NC (US); Brian J. Mosley, Raleigh, NC (US)

(73) Assignee: BioLink Life Sciences, Inc., Cary, NC (US)

( * ) Notice: Subject to any disclaimer, the term of this patent is extended or adjusted under 35 U.S.C. 154(b) by 430 days.

(21) Appl. No.: 12/506,408

(22) Filed: Jul. 21, 2009

(65) Prior Publication Data

US 2011/0021629 A1    Jan. 27, 2011

(51) Int. Cl.
*C07F 9/09* (2006.01)
*A61K 31/295* (2006.01)

(52) U.S. Cl. .......................................... 556/17; 514/502

(58) Field of Classification Search ................... 514/502; 556/17

See application file for complete search history.

(56) References Cited

U.S. PATENT DOCUMENTS

| | | | |
|---|---|---|---|
| 6,903,235 B2 | 6/2005 | Hsiao et al. | |
| 7,816,404 B2 | 10/2010 | McCall et al. | |
| 2008/0274210 A1 | 11/2008 | Chan et al. | |
| 2009/0023686 A1 | 1/2009 | McCall et al. | |
| 2009/0028962 A1 | 1/2009 | Bortz et al. | |
| 2009/0035385 A1 | 2/2009 | Bortz et al. | |
| 2009/0186939 A1 | 7/2009 | Chan et al. | |

FOREIGN PATENT DOCUMENTS

WO    2007/089571    8/2007

OTHER PUBLICATIONS

Fidler et al., 2004, "A Micronized, Dispersible Ferric Pyrophosphate with High Relative Bioavailability in Man", British Journal of Nutrition, 91: 107-112.

*Primary Examiner* — Porfirio Nazario Gonzalez

(74) *Attorney, Agent, or Firm* — Casimir Jones SC

(57) ABSTRACT

New iron preparations comprising stable, unpolymerized iron(III) citrate complex compositions and methods for their preparation are provided. Further, the invention involves the use stable, unpolymerized iron(III) citrate complex compositions of the invention as a food additive, nutritional supplement, dietary supplement, medical food, nutrient, iron fortificant, and source of iron in the fields of nutrition for humans, animals, fish, and birds and of diagnostics. The invention further involves the use of stable, unpolymerized iron(III) citrate complex compositions of the invention as a pharmaceutical and pharmacologically active ingredient for human clinical and veterinary applications.

13 Claims, 1 Drawing Sheet

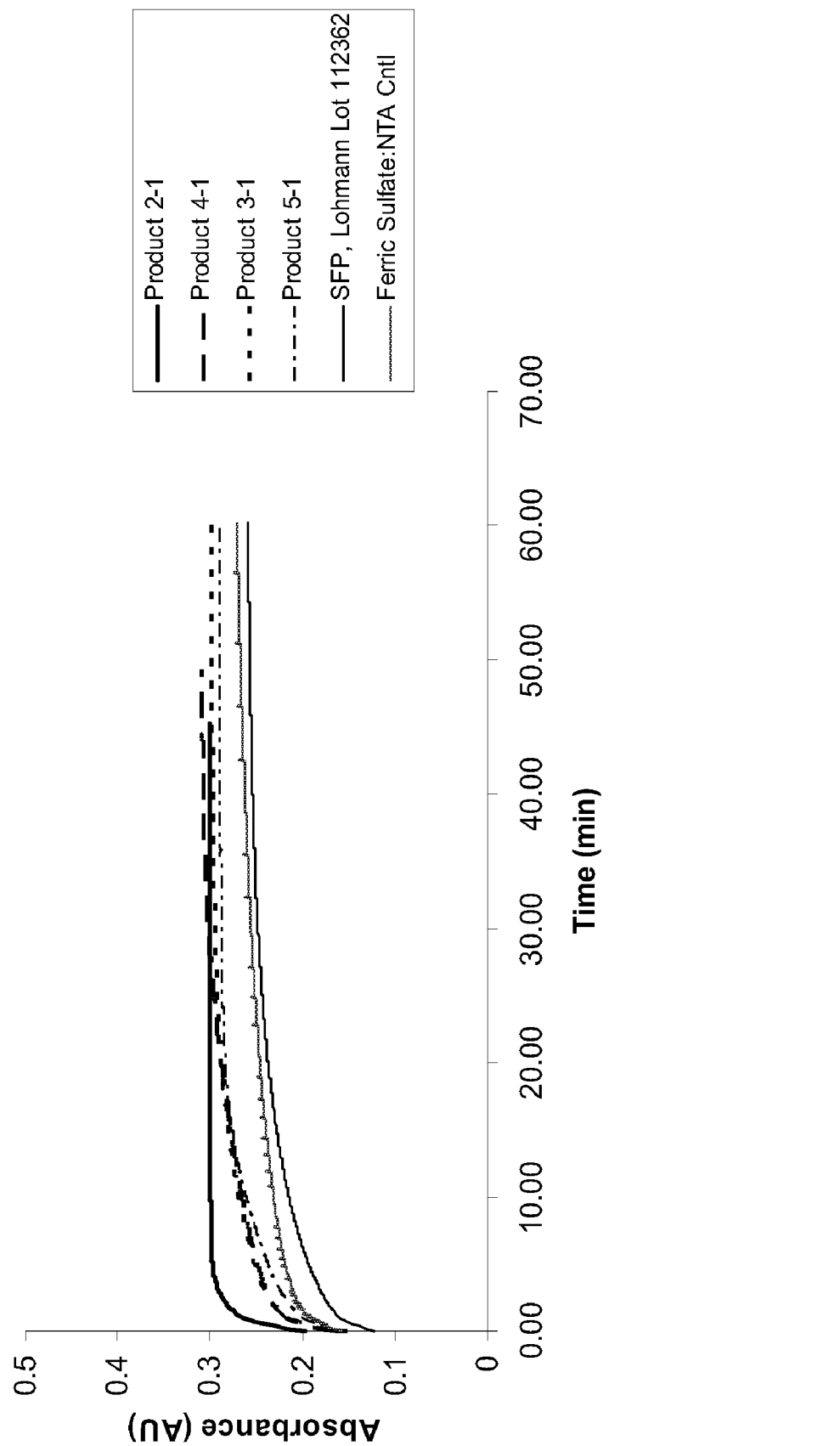

IRON PREPARATION SUITABLE FOR PHARMACEUTICAL FORMULATION AND PROCESS FOR THE PREPARATION THEREOF

BACKGROUND OF THE INVENTION

Iron deficiency is the most common micronutrient deficiency in the world, affecting 1.3 billion people (24% of the world's population). Severe iron deficiency, i.e., iron deficiency anemia, is particularly debilitating, since iron has several vital physiological functions, including: (1) carriage of oxygen from lung to tissues; (2) electron transport within cells; and (3) participation as a co-factor of essential enzymatic reactions in neurotransmission, synthesis of steroid hormones, synthesis of bile salts, and detoxification processes in the liver. Among the consequences of iron deficiency anemia are an increase maternal & fetal mortality, an increased risk of premature delivery and low birth weight, learning disabilities & delayed psychomotor development, reduced work capacity, impaired immunity (high risk of infection), an inability to maintain body temperature, and an associated risk of lead poisoning because of pica.

Iron deficiency anemia commonly affects patients having chronic diseases, such as kidney disease, inflammatory bowel disease, cancer, HIV, and diabetes. Iron deficiency also afflicts mammals after blood loss and females after parturition.

It is well known to treat an iron deficiency with orally administered iron supplements. In general, relatively large doses of oral iron fortificants are needed to achieve a desired therapeutic effect. The absorption of non-heme iron from the gastrointestinal tract varies from 2% to greater than 90% because it is strongly influenced by the iron status of the body, the solubility of the iron salts in aqueous solutions, the integrity of gut mucosa, and the presence of absorption inhibitors or facilitators in ingesta. For example, foods which contain polyphenol compounds and/or phytic acid bind with dietary iron, decreasing the concentration of free iron in the gut and forming complexes that are not absorbed. Cereals such as wheat, rice, maize, barley, sorghum and oats; vegetables such as spinach and spices; legumes such as soya beans, black beans, and peas; and beverages such as tea, coffee, cocoa and wine contain substances that inhibit iron absorption from the gut. Likewise, L-ascorbate and L-cysteine are known to facilitate absorption of ferrous iron.

Oral administration of iron supplements is known to be commonly accompanied by undesirable side effects, including nausea, vomiting, gastric irritation, constipation, and black stools. For these and other reasons, patient noncompliance with dosage regimens is also a common problem. In addition, conventional iron fortificants present safety concerns, since intolerance to conventional iron salts and accidental overdosing of iron is one of the leading causes of hospitalization in adults and children and is a leading cause of death children under the age of six.

Ferric Citrate. Ferric citrate (Chemical Abstracts Registry No. 12338-05-8) is an iron(III) citrate salt composed of ferric iron and citrate ions in an undefined molecular composition. Ferric citrate is used as an iron fortificant and hematinic agent. [*The Merck Index*, 14$^{th}$ Ed., M. J. O'Neil, P. E. Heckelman, C. B. Koch, K. J. Roman, Eds. Merck & Co., Inc., Whitehouse Station, N.J., 2006, Monograph No. 4021, page 687.]

When freshly prepared by reaction of an iron(III) salt and citric acid in solutions having a low pH, ferric citrate is a 1:1 iron:citrate complex that is green in color and has a weight percent composition of about 17.9% iron(III) and 62.2% citrate. (The other 20 weight percent of the composition consists of water and other anions and amines derived from the iron salt.) [*Structure and Bonding, Volume* 6. P. Hemmerich, C. K. Jørgensen, J. B. Neilands, R. S. Nyholm, D. Reinen, and R. J. P. Williams, Eds. Springer-Verlag, New York, pages 132-134.] Ferric chloride, ferric sulfate, and ferric nitrite are examples of iron(III) salts having a low pH, and U.S. Pat. No. 6,903,235 confirms in its disclosures that a pharmaceutical-grade ferric citrate having a weight percent composition of about 17.9% iron(III) and 62.2% citrate (a 1:1 complex of iron and citrate) is formed by reacting ferric chloride, ferric sulfate, or ferric nitrite with citric acid in alcohol solution.

During storage the chemical composition of the ferric citrate complex does not change. However, even when protected from light, the physical characteristics of ferric citrate change significantly. For example, the color of ferric citrate changes from green to garnet red or pale brown. In addition, the solubility of the complex changes from water soluble to water insoluble. It has long been known that these and other physical changes mark a change in composition from low molecular weight complexes having a formula weight of less than about 1,000 Daltons to high molecular weight polymers having formula weights estimated at greater than 10,000 Daltons. [*Structure and Bonding, Volume* 6. P. Hemmerich, C. K. Jørgensen, J. B. Neilands, R. S. Nyholm, D. Reinen, and R. J. P. Williams, Eds. Springer-Verlag, New York, 1969, pages 132-134.] Ferric citrate polymers are spherical in shape when examined by electron microscopy, and the iron ions are tightly bound to bridging oxygen atoms, not citrate, and buried deep within the sphere. Citrate is believed to be located at the surface of the spheres, where it acts to stabilize the surface of the oxy-iron polymer, prevent additional cross-linking and polymerization to chemical entities having molecular weights that greatly exceed 10,000 Daltons, and prevent precipitation of the polymers formed thereby at high pH.

Polymerization of ferric citrate also adversely changes the biological properties and bioavailability of the ferric citrate complex. In fact, the biological properties and bioavailability of polymeric ferric citrate more closely resemble those of ferritin, the physiological storage form of iron, than physiologically bioavailable iron, as in iron salts such as ferrous sulfate. For example, only a small percentage iron from polymeric ferric citrate is available to cross membranes. [*Structure and Bonding, Volume* 6. P. Hemmerich, C. K. Jørgensen, J. B. Neilands, R. S. Nyholm, D. Reinen, and R. J. P. Williams, Eds. Springer-Verlag, New York, 1969, pages 132-134.] Likewise, Gebran et al. have reported that iron polymers significantly impair the immune response in mammals. [S. J. Gebran, E. L. Romano, A. Soyano. Iron polymers impair the function and maturation of macrophages. Immunopharmacol Immunotoxicol 1993; 15(4): 397-414.] For example, Gebran et al. reported that the phagocytic capacity of ferric citrate-treated macrophages was inhibited in a dose-related manner. Cell viability was not affected, although the level of lipid peroxidation, an undesirable change to the lipids and lipid membrane, was significantly elevated as the result of exposure. Further, the capacity of low density, nonadherent bone marrow cells to form colonies of macrophages was also inhibited significantly by polymerized ferric citrate. In a second study, this research group found that polymerized ferric citrate suppressed the PHA-induced proliferative response and E. rosette formation of human lymphocytes in culture. [(a) A. Soyano, H. Pons, R. Montano, E. Roman, A. Muller-Soyano, R. Somoza. Effect of iron compounds on the immune response in vitro. Recent Adv Pharm Therapy 1989; p. 401; (b) A. Soyano, E. Fernandez, E. Romano. Suppressive effect of iron on the in vitro lymphocyte function: Formation of iron polymers as a possible explanation. Int Arch Allergy Appl Immunol 1985; 76:376; (c) A. Soyano, H. Pons, E. L. Romano. Interaction of iron polymers with blood mononuclear cells and its detection with the Prussian blue reaction. Immunopharmacol 1992; 23: 29.]

Once formed, high molecular weight ferric citrate polymers are very slow to dissociate to low molecular weight chemical entities that provide iron. It is known that the bioavailability of iron from ferric citrate polymers is very low. For example, Bates et al. showed that ferric iron from ferric citrate is transferred to transferrin, the physiological iron transporter, over a matter of days. [G. W. Bates, C. Billups, P. Saltman. The kinetics and mechanism is iron(III) exchange between chelates and transferrin. I. The complexes of citrate and nitrilotriacetic acid. J Biol Chem 1967; 242(12): 2810-2815.] It would be desirable to provide an iron complex that would transfer iron within minutes or hours.

It is known that polymerization of freshly prepared ferric citrate can be prevented or slowly reversed under certain conditions. For example, if a 20-fold excess of citrate is present in a solution of freshly prepared ferric citrate, polymerization of the ferric citrate will be suppressed. Likewise, a 20-fold excess of citrate in solution will reverse polymerization over a period of many days. Polymerization is also reversed over a period of hours to days by the addition of amino-acetate iron-chelating agents such as NTA or EDTA. [*Structure and Bonding, Volume* 6. P. Hemmerich, C. K. Jørgensen, J. B. Neilands, R. S. Nyholm, D. Reinen, and R. J. P. Williams, Eds. Springer-Verlag, New York, 1969, pages 132-134.]

Since the absorption of non-heme iron from the gastrointestinal tract (i.e., its oral bioavailability) is strongly influenced by the solubility of the iron salts in water and the availability of the iron for interaction with physiological iron receptors, such as the divalent metal transporters on enterocytes, and physiological iron transporters, such as transferrin, there is a long-felt need for a stable, bioavailable, unpolymerized form of ferric citrate that is utilized physiologically after oral or parenteral administration. The present invention provides an iron preparation having those properties.

SUMMARY OF THE INVENTION

The present invention provides iron preparations suitable for pharmaceutical formulation and processes for the preparation thereof. An iron preparation of the invention comprises a stable, unpolymerized iron(III) citrate complex composition that is prepared by oxidation of iron(II) citrate dibasic in the presence of dihydrogen disodium pyrophosphate in water. A ferric citrate complex composition of the invention comprises citrate and pyrophosphate chelated to ferric iron in a manner that prevents polymerization and the undesirable chemical changes that result from polymerization. Compositions of the invention distinguish from iron(III) citrates which are previously known by having a completely different structural composition and exhibiting a stability and ability to provide iron that is significantly greater than iron(III) citrates of the art.

Formulations of stable, unpolymerized iron(III) citrate complex compositions of the invention provide iron in a form that is useful as an iron fortificant, hematinic agent, and useful treatment of iron deficiency anemia, particularly the anemia of chronic disease. Further, stable, unpolymerized iron(III) citrate complex compositions of the invention provide iron in a form that is useful for chemical and biological applications other than biomedical applications.

These and other features, advantages and objects of the present invention will be further understood and appreciated by those skilled in the art by reference to the following specification, claims and appending drawings.

DESCRIPTION OF THE DRAWINGS

FIG. 1 is a graph illustrating the rate and extent of uptake by human apotransferrin of iron from iron preparations of the invention and from known iron salts [soluble ferric pyrophosphate (SFP), Paul Lohmann GmbH, Emmerthal, Germany; ferric sulfate (as the ferric sulfate:NTA chelate)].

DETAILED DESCRIPTION OF THE INVENTION

The main object of the invention is to provide iron preparations suitable for pharmaceutical formulation and processes for the preparation thereof. Other objects and advantages of the invention are set out herein or are obvious therefrom to one skilled in the art. The objects and advantages of the invention are achieved by the compounds and processes of the invention.

The invention provides iron preparations suitable for pharmaceutical formulation into dosage forms that provide physiologically bioavailable iron. For example, iron preparations of the invention provide iron for transfer to physiological receptors for iron, including divalent metal transporters and apotransferrin.

The invention also involves processes for the preparation of said iron preparations, comprising oxidation of iron(III) citrate dibasic in the presence of dihydrogen disodium pyrophosphate in water. The iron preparation that is prepared by this process is a yellow-green solid having, by weight, from about 9% to about 14% iron, from about 30% to about 60% citrate, from about 5% to about 20% pyrophosphate, and from about 1% to about 15% sodium. The iron preparation is a stable, unpolymerized iron(III) citrate complex that is bioavailable after oral or intravenous administration (i.e., the iron preparation provides iron to the body of a mammal).

Further, the invention involves the use of an iron preparation of the invention as a food additive, nutritional supplement, dietary supplement, medical food, nutrient, iron fortificant, and source of iron in the fields of nutrition for humans, animals, fish, and birds. The invention further involves the use of an iron preparation of the invention as a pharmaceutical and pharmacologically active ingredient in pharmaceutical formulations for human clinical and veterinary applications. The invention also involves the use of iron preparations of the invention for diagnostics and as a source of iron for chemical and biological systems that require iron.

The invention further comprises a method of administering an iron preparation of the invention to a subject in need of such administration for the prevention or treatment of iron deficiency or anemia.

According to the method of the present invention, said iron preparation is administered, alone or in combination with other substances (e.g., along with materials necessary to form a tablet, caplet, pill, capsule, troche, lozenge, powder, granulate, or solution that is suitable for ingestion) in sufficient quantities to prevent the onset or reverse the course of deleterious effects brought about by iron deficiency. Further, according to the method of the present invention, an iron preparation of the invention is administered, alone or in combination with other substances, in sufficient quantities in a formulation for parenteral administration to prevent the onset or reverse the course of deleterious effects brought about by iron deficiency.

In the method of the present invention, an iron preparation as described hereinabove is administered to a mammal by oral ingestion or injection. The composition, so administered, may be regarded either as a food additive, a substance that is generally regarded as safe (i.e., a GRAS substance), or a drug within the meaning of Title 21 of the Code of Federal Regulations (CFR).

In the method of the present invention, an iron preparation as described hereinabove may be ingested as a food supplement, dietary supplement, nutritive supplement, or medical food. By the terms "food supplement, dietary supplement, and nutritive supplement" is meant that a composition of the present invention exogenously augments the iron that is present in food, components of the diet, and compositions intended to provide nutrition. By the term "medical food" is meant that an iron composition of the present invention is prescribed by a clinician for the purpose of exogenously augmenting iron in ingesta.

In the method of the invention, an iron preparation as described hereinabove may be administered as a drug either orally or by injection.

Included within the scope of this invention is a method of treating iron deficits in a warm-blooded animal using pharmaceutical compositions comprising an iron preparation of the invention and a suitable pharmaceutical carrier. For the purpose of this disclosure, a warm-blooded animal is a member of the animal kingdom which includes but is not limited to mammals and birds. The most preferred mammal of this invention is human.

The term "complex" as used herein generally means a metal cation and anions that surround the metal cation and are joined to it by electrostatic bonds. An iron preparation of the invention comprises an iron complex that is prepared by oxidation of iron(II) citrate dibasic in the presence of dihydrogen pyrophosphate in water. The complex comprises ferric iron cations surrounded by and joined by electrostatic bonds to both citrate and pyrophosphate in a manner that prevents polymerization.

The term "excipient material" means any compound forming a part of the formulation which is not intended to have biological activity itself and which is added to a formulation to provide specific characteristics to the dosage form, including by way of example, providing protection to the active ingredient from chemical degradation, facilitating release of a tablet or caplet from equipment in which it is formed, and so forth.

The terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; (c) relieving the disease, causing regression of the disease and/or its symptoms or conditions; or (d) returning a clinical value to the concentration range normally found in a subject.

The phrase "therapeutically effective" is intended to qualify the amount of for use in an orally or intravenously administered therapy which will achieve the goal of abating, mitigating, reducing or preventing, for example, an iron deficiency disorder, or of restoring physiologically adequate concentrations of iron while avoiding adverse side effects typically associated with conventional iron compositions.

The terms "sterile" and "sterilized" as used herein have their conventional meanings as understood by skilled artisans when referring to the sterility required pharmaceutically for intravenous preparations. Sterilization is achieved conventionally, either by application of heat (e.g., high-pressure steam sterilization or high-temperature short time steam sterilization) or through the use of filters having a pore-size sufficiently small to exclude pathogens.

The term "suitable for intravenous injection" as used herein has its conventional meaning as understood by skilled artisans when referring to a composition that meets the general requirements for solutions for injection as presented in the General Chapter of the U.S. Pharmacopoeia entitled "Injections." (U.S. Pharmacopoeia, U.S. Pharmacopoeial Convention, Inc., Rockville, Md., 2006.)

The term "parenteral nutrition composition" means a hyperalimentation composition for intravenous administration comprising one or more components selected from the group consisting of a carbohydrate solution, an amino acids solution, and lipid.

By the term "physico-chemically compatible" with respect to a component of a parenteral nutrition composition is meant that a disruption of the composition is not observed, as determined by the observation of phase separation, creaming, particulate formation, an increase in the percentage of lipid globules having a diameter greater than 5 μm as measured by conventional light scattering, light obscuration, or particle-sizing techniques, or the like.

The term "dialysis therapy" means the clinical treatment of chronic kidney disease comprising the osmotic exchange of metabolites, toxins and water across a membrane from a renal disease patient's blood to a dialysate solution. Conventional dialysis therapy is described by S. Pastan and J. Bailey in the article entitled "Dialysis therapy" published in The New England Journal of Medicine, volume 338, number 20, pages 1428-1437 (1998).

The term "dialysate" means a composition for intravenous administration as part of a dialysis procedure for the treatment of chronic kidney disease. Dialysate is conventionally provided for use in either peritoneal dialysis (in which the peritoneal membrane constitutes the dialysis membrane) or hemodialysis (in which a synthetic membrane constitutes the dialysis membrane). Hemodialysate is generally prepared from two dry powder concentrates, the acid ("A") and base ("B") concentrates, which are reconstituted in treated water before use, or from two aqueous solutions of the A and B dry powder concentrates. The A concentrate, containing an organic acid and electrolytes and osmotic agents other than bicarbonate, is mixed with B concentrate containing bicarbonate and treated water in a dialysis machine to make the final hemodialysate. Peritoneal dialysate is a premixed solution of osmotic agents, electrolytes, and water that is used in dialysis without further constitution.

It is understood that any and all whole or partial integers between any ranges set forth herein are included herein.

After diligent and lengthy experimentation, the inventor has discovered a process for the preparation of an iron complex comprising stable, unpolymerized iron(III) citrate complex compositions comprising, by weight, about 9% to about 14% iron, from about 30% to about 60% citrate, from about 5% to about 20% pyrophosphate, and from about 1% to about 15% sodium.

The method for the preparation of said iron preparation comprises combining ferrous citrate dibasic and disodium dihydrogen pyrophosphate in water, exposing the resulting mixture to oxygen in a volume sufficient to oxidize the ferrous iron to ferric iron and at a rate sufficiently slow to allow complex formation between iron(III), citrate, and pyrophosphate as oxidation occurs, thus preventing polymerization of ferric citrate, and isolating a stable, unpolymerized iron(III) citrate complex therefrom by removing water. The reaction mixture may be exposed to oxygen by known means including, by way of example, bubbling, aerating, or sparging.

The inventor has discovered that the following reaction parameters of the method require careful control: (a) the raw material, (b) the purity of each raw material; (c) the ratio of ferrous citrate to disodium dihydrogen pyrophosphate; (d) the rate of oxidation; and (e) the temperature during removal of water.

The inventor has discovered that only ferrous citrate dibasic is a useful raw material for the preparation of a stable, unpolymerized iron(III) citrate complex of the invention. If other iron salts are used in the preparation, iron compositions are obtained having physical and chemical properties different from an iron preparation of the invention. For example, even when combined with citric acid or its salts, ferrous salts other than ferrous citrate dibasic fail to provide a stable, unpolymerized iron(III) citrate complex of the invention that is free of other anionic ligands. For example, if ferrous sulfate or ferric sulfate is used as the iron-containing raw material in the preparation, the iron product that is obtained contains sulfate. Likewise, if ferrous or ferric ammonium salts are used as the iron-containing raw material in the preparation, the iron product that is obtained contains ammonia in the final product. Even when combined with citric acid or its salts, ferric citrate fails to provide a stable, unpolymerized iron(III) citrate complex of the invention. Ferric pyrophosphate is unreactive with citric acid or citrate salts in water.

Further, the inventor has discovered that only disodium dihydrogen pyrophosphate is a useful raw material for the preparation of an iron preparation of the invention. Tetrasodium pyrophosphate, pentasodium tripolyphosphate, and other phosphate or polyphosphate salts fail to provide an iron preparation of the invention.

The inventor has also discovered that each raw material must exhibit high purity. The ferrous citrate dibasic and disodium dihydrogen pyrophosphate must contain less than about 250 micrograms per gram of each of the elements aluminum, antimony, arsenic, bismuth, cadmium, copper, lead, mercury, molybdenum, thallium, and tin, since these metals exhibit known toxicities in humans. The pyrophosphate must contain less than about 0.1% phosphate, and preferably less than about 0.01% phosphate.

Likewise, the inventor has discovered that oxygen is a suitable oxidant and may be introduced into the reaction mixture by conventional means, including, by way of example, bubbling, aerating, sparging, or oxygen-generation in situ. However, careful control of the rate of oxidation of ferrous citrate dibasic is required. If oxidation of ferrous citrate to ferric citrate occurs too rapidly, ferric citrate polymerizes before iron ligation to pyrophosphate occurs. For example, if oxidation is carried out using pure oxygen gas or 40% hydrogen peroxide, as opposed to air, the oxidation of ferrous citrate to ferric citrate occurs too rapidly, and ferric citrate polymerizes, even in the presence of the most preferred ratio of disodium dihydrogen pyrophosphate to iron citrate. The inventor has found that air oxidation (i.e., about 21% oxygen) is suitable and provides the desired stable, unpolymerized ferric citrate composition in quantitative yield after 4-10 days of reaction. Oxidation with gasses containing a lower percentage of oxygen proceeds significantly more slowly, and it is expected that a gas containing less than about 5% oxygen will oxidize the ferrous citrate so slowly as to be an impractical method of preparation.

The inventor has discovered that control of the temperature during water removal is critical. The most preferred method of removing volatile solvents is removal of water by sublimation or lyophilization, because this condition employs the lowest temperatures and highest vacuums for removal of water, factors which shorten the time required for water removal in its entirety. In the alternative, evaporation of water under vacuum is useful for removal of water, provided that the temperature is maintained below about 80° C., more preferably below about 75° C., and most preferably below about 70° C.

The inventor has also discovered that limiting the volume of water that is employed to the minimum volume required to dissolve the final product is advantageous. All of the water used in the reaction is removed by evaporation under vacuum to isolate the product. If large volumes of water are used, additional time and energy must be expended to remove all of the solvent.

Further, the inventor has discovered that preventing microbial contamination during the preparation and isolation of an iron composition of the invention is advantageous. Iron is a nutrient for microorganisms and promotes their growth. Preventing microbial contamination is accomplished by passing both solutions of the raw materials and solutions of the product through filters having a pore-size sufficiently small to prevent passage of microbial contaminants.

The inventor has discovered that use of a molar ratio of $Fe^{2+}$ as (ferrous citrate dibasic) to pyrophosphate (as disodium dihydrogen pyrophosphate) of about 2:1 to 5:1 provides stable, unpolymerized iron(III) citrate complexes of the invention.

Further, the inventor has discovered that the pH of a solution of an iron preparation of the invention in water may be adjusted from about 2-3, the pH determined in the solution in which the iron preparation is first prepared, to a pH of about 5 by the dropwise addition of 1 N sodium hydroxide solution. Adjustment of pH in this manner requires the addition of about 1 mL of 1 N NaOH for each millimole of iron preparation. A dark green, almost black, solution is obtained after pH adjustment in this manner. An iron preparation of the invention is isolated by removal of the water in the manner described above.

If pH adjustment of a solution of an iron preparation of the invention in water is performed as disclosed above, iron preparations of the invention having a molar ratio of $Fe^{2+}$ as (ferrous citrate dibasic) to pyrophosphate (as disodium dihydrogen pyrophosphate) of about 2:1 exhibit the most desirable chemical properties. Iron preparations of the invention having a molar ratio of $Fe^{2+}$ as (ferrous citrate dibasic) to pyrophosphate (as disodium dihydrogen pyrophosphate) of about 2:1 maintain high water solubility during and after pH adjustment to about pH 5 and are most preferred. In contrast, a fraction of the composition of an iron preparations of the invention having a molar ratio of $Fe^{2+}$ as (ferrous citrate dibasic) to pyrophosphate (as disodium dihydrogen pyrophosphate) of about 5:1 is water-insoluble after pH adjustment to about pH 5. The results of these experiments indicate that pH adjustment in the pH range from 3 to 5 of iron preparations of the invention having a molar ratio of $Fe^{2+}$ as (ferrous citrate dibasic) to pyrophosphate (as disodium dihydrogen pyrophosphate) of about 3:1, about 4:1, and about 5:1 will result in iron preparations that are less water-soluble than is preferred.

While not wishing to be bound by any particular hypothesis or theory, the inventor hypothesizes that the mechanism of formation of a stable, unpolymerized iron(III) citrate complex of the invention comprises a slow oxidation of ferrous citrate to ferric citrate by air. As ferric citrate is formed, pyrophosphate, which has a high affinity for ferric iron, is ligated to the newly formed ferric citrate, thus providing a stable ferric citrate pyrophosphate complex that does not polymerize. (The strength of the electrostatic bond between a ligand and a metal ion is conventionally described by a stability constant, $K_{stab}$, and frequently expressed as the logarithm of that constant. [Martell A E, Smith R M. Critical Stability Constants. Volumes 1-6. New York: Plenum Press; 1974, 1975, 1976, 1977, 1982, and 1989.] The log $K_{stab}$ for ferric iron and citrate and that for ferric iron and pyrophosphate is 12 and 22.2, respectively. [Gupta A J, Crumbliss A L. Treatment of iron deficiency anemia: Are monomeric iron compounds suitable for parenteral administration? J Lab Clin Med 2000; 136: 371-378.]) This theory is supported by the observation that if a method of preparation is used that differs from the method of preparation of the invention, an iron-containing product is obtained that is different from the iron preparation of the invention. Likewise, if an iron-containing raw material is used that differs from iron(II) citrate dibasic, an iron-containing product is obtained that is different from the iron preparation of the invention.

According to the present invention, an iron preparation of the invention can be recovered from a solution of ferric ion, citrate, and pyrophosphate by removal of water. Thus, an iron preparation of the invention is recovered from the solution if, after a reaction time sufficient to provide a solution of an iron preparation of the invention, the water is removed.

The methods for the preparation of an iron preparation of the invention as disclosed herein are advantageously useful in pharmaceutical manufacturing of these compositions, as illustrated by way of example, by the following. The raw materials and solvents are commercially available. Advantageously, from an industrial perspective, the process for the preparation of the aforesaid solid compositions involves the use of conventional apparati and reagents. The reaction conditions enable control of reaction temperature, monitoring of the progress of reaction for extent of completion, and convenient and high yield steps for the recovery of the desired iron preparations from the aqueous solution in which they are formed. The methods of preparation provide for removal of microorganisms that may adventitiously contaminate the product after formation of an iron preparation of the invention in solution and prior to the removal of water. However, because the methods of preparation does not provide for removal of chemical contaminants, the quality and purity of the starting materials, including water, must be rigorously controlled and must meet reagent grade standards, pharmaceutical grade standards, or higher standards for purity and freedom from chemical contaminants.

The iron preparations obtained by the methods of the present invention exhibit reproducible composition, an absence of both solvents and chemical and biological contaminants, and stability, qualities qualifying the iron preparations for use in pharmaceutical formulations. Further, the iron preparations of the present invention are easily milled or processed into formulary dosage forms using conventional methods and techniques.

Iron preparations obtained by the methods of the present invention exhibit physico-chemical stability during lengthy storage at ambient temperatures. By this property, as well as by other properties disclosed further below, iron preparations of the invention distinguish from iron(III) citrates which are previously known.

Dosage Forms and Therapeutic Uses of Compounds of the Present Invention. The compositions of this invention can be administered by any means that effects contact of the therapeutically active ingredients (i.e., active ingredients) with the site of action in the body of a warm-blooded animal. A most preferred administration is by the oral route (i.e., ingestion). The active ingredients can be administered by the oral route in solid dosage forms, such as tablets, capsules, powders, chewable compositions, and rapidly dissolving film, or in liquid dosage forms, such as elixirs, syrups, and suspensions. The composition is preferably made in the form of a dosage unit containing a particular amount of each active ingredient. Capsules or tablets for oral administration may contain a controlled-release formulation as may be provided in a dispersion of active compound in hydroxypropyl methylcellulose or related material known to alter the kinetics of release of the active agent. Solid dosage forms can be manufactured as sustained release products to provide for continuous release of medication over a period of hours using known pharmaceutical techniques. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

A second preferred administration is by the intravenous route. The active ingredients can be administered by the intravenous route in liquid dosage forms, such as solutions, suspensions, or emulsions. The composition is preferably made in the form of a dosage unit containing a particular amount of each active ingredient.

By way of example, parenteral nutrition (PN), also known as parenteral hyperalimentation, is a medical treatment that supplies nutrition-maintaining compositions intravenously, and is indicated for a variety of mammalian disorders, such as cancer, gastrointestinal diseases, major body burns, extensive wounds, and AIDS. Partial parenteral nutrition supplies only part of daily nutritional requirements, supplementing oral intake. Many hospitalized patients receive dextrose or amino acid solutions by this method. Total parenteral nutrition treatment (TPN) supplies all daily nutritional requirements intravenously, circumventing the gut. TPN may be employed following surgery, when feeding by mouth or using the gut is not possible, when a patient's digestive system cannot absorb nutrients due to chronic disease, or, if nutrition cannot be met by enteral feeding and supplementation. Premature and sick infants often require extended periods of TPN. Compositions for parenteral nutrition generally contain at least water, glucose, amino acids, and optionally emulsified fats. They may be aseptically compounded from amino acid solutions, dextrose solutions, and/or lipid emulsions. PN compositions may further contain vitamins, electrolytes and essential trace elements. The inventors have discovered that a soluble ferric pyrophosphate composition of the present invention is compatible with PN compositions and when admixed with a PN composition provides supplemental iron and pyrophosphate. Supplemental iron and pyrophosphate are useful, by way of example, to treat iron deficiency (anemia) and bone disorders, respectively, in humans and other warm-blooded animals.

Likewise, dialysis is a clinical treatment procedure by which metabolic by-products, toxins, and excess fluid are removed from the blood of a subject with chronic kidney disease (CKD) by transfer across a dialysis membrane. Dialysis may be conventionally performed as hemodialysis, in which a synthetic membrane constitutes the dialysis membrane, or as peritoneal dialysis, in which a patient's peritoneal membrane constitutes the dialysis membrane. Dialysis-related iron deficiency affects about 90 percent of CKD patients by six months of treatment, and the inventor expects that a ferric pyrophosphate citrate chelate composition of the invention may be substituted for convention iron fortificants that are administered to CKD patients undergoing dialysis.

Iron-deficiency (or more severely, iron deficiency anemia) is commonly diagnosed as a reduction in the number of red blood cells or a reduction in one or more of the major red blood cell (RBC) measurements, such as hemoglobin (Hb), hematocrit (Hct), RBC count, or RBC morphology. Most frequently, the patient is a child, a woman of child-bearing age, a person of Mexican or black heritage, an elderly person, or a person with a chronic disease. Others at risk for iron-deficiency anemia include blood donors, those of low socio-economic status, postpartum females, women with heavy menstrual cycles, and those consuming vegetarian diets.

Iron deficiency results when iron demand by the body is not equivalent to iron obtained from the diet. For normal homeostasis, about 5% to 10% of dietary iron absorption occurs in the jejunum. States of iron overload cause this amount to decrease, while states of iron deficiency can increase three- to five-fold. Dietary iron is found in two forms: heme and non-heme. The heme form comes primarily from meat, fish, and poultry; the non-heme form is found mostly in plants, dairy foods, and as iron fortificants supplied in oral supplements. Non-heme iron is the more prominent source of iron, both in the diet and in iron supplements. Absorption of non-heme iron from the gastrointestinal tract involves iron-binding by divalent metal transporter enzymes on enterocytes, iron transport into the cells, and iron-binding to transferrin, the physiological protein involved in iron transport and distribution in the circulatory system.

To demonstrate that an iron preparation of the invention provides iron in a form that can be used physiologically (i.e., a form that can be bound to divalent metal transporter enzymes and to transferrin), in vitro studies were completed to determine the rate and extent of iron uptake by Caco-2 cells and human apotransferrin when each test system was exposed to an iron preparation of the invention.

The Caco-2 cell line is a human adenocarcinoma cell line that has proven to be a useful model for studying iron bioavailability from foods and iron fortificants. [Glahn R P, Lee O A, Yeung A, Goldman M I, Miller D D. Caco-2 cell ferritin formation predicts nonradiolabeled food iron availability in an in vitro digestion/Caco-2 cell culture model. J Nutr 1998; 128: 1555-1561. Glahn R P, Wien E M, Van Campen D R, Miller D D. Caco-2 cell iron uptake from meat and casein digests parallels in vivo studies: Use of a novel in vitro method for rapid estimation of iron bioavailability. J Nutr 1996; 126: 332-339.] The cells differentiate into polarized monolayers with characteristics such as a brush border membrane containing the enzymes present in normal absorptive epithelial enterocytes. [Conrad M E, Umbreit J N. A concise review: iron absorption—the mucin, mobilferrin-integrin pathway. A competitive pathway for metal absorption. Am J Hematol 1993; 42: 67-73.] Ferritin formation by Caco-2 cells following exposure to an iron source is used as a marker for iron uptake and provides translational evidence of oral bioavailability to humans and other mammals.

The major iron transport pool in human serum is iron bound to apotransferrin, an 80 kDa bilobal protein with two iron binding sites. The function of apotransferrin is: i) to bind iron and as transferrin (iron-laden apotransferrin) move iron from storage depots (ferritin) to various cell receptors; ii) to prevent iron from engaging in redox reactions which produce toxic free radicals; and iii) to prevent bacterial acquisition of this essential nutrient. Consequently, the best way to introduce iron into the normal metabolic pool is to deliver it to apotransferrin. A physico-chemical measurement of the bioavailability of Fe(III) in an iron preparation of the invention is the kinetic efficiency with which the preparation loads Fe(III) into apotransferrin in aqueous solution at physiological pH 7.4. Therefore, we measured the kinetics of Fe-transferrin formation from iron preparations of the invention and compared the kinetics to the kinetics of Fe-transferrin formation from commercial soluble ferric pyrophosphate and ferric sulfate-NTA complex at identical conditions according to the method of Bates, et al. [Bates, G. W., Billups, C. Saltman, P.: The Kinetics and Mechanism of Iron (III) Exchange between Chelates and Transferrin. J Biol Chem; 242 (12): 2810-2815.] Experimental data are shown in FIG. 1 and verify that iron from an iron preparation of the invention is taken up by human apotransferrin more rapidly than and with the same near quantitative efficiency as from known iron salts, such as soluble ferric pyrophosphate (SFP; Paul Lohmann GmbH, lot 112362, a commercial material) and ferric sulfate-NTA chelate (a control material known to transfer iron rapidly and completely to transferrin). These data verify that an iron preparation of the invention is bioavailable.

Treatment for iron deficiency anemia commonly involves promotion of erythropoiesis, the process by which red blood cells (RBCs) and the hemoglobin within these cells are produced. Maintenance of optimal RBC count occurs via erythropoietin, a protein that stimulates stem cell differentiation, increases the rate of mitosis, increases release of reticulocytes from the bone marrow, and increases hemoglobin formation. Important vitamins and minerals involved in the erythrocyte process include iron, vitamin $B_{12}$, and folic acid. Iron's primary role is incorporation into hemoglobin, a key component of RBC function. Folic acid helps with synthesis of DNA and RNA along with maturation of erythrocytes, while vitamin $B_{12}$ (cobalamin) is involved with synthesis of DNA, maturation of erythrocytes, and facilitation of folate metabolism. A deficiency of any of these components impairs the transport of oxygen and normal hematologic processes.

The treatment goal of iron deficiency anemia is to correct the underlying cause of the anemia as well as to provide iron sufficient for repletion of iron stores and normalization of Hb and Hct. First-line therapy for most patients is the administration of oral iron. Different forms of iron contain varying levels of elemental iron. It is generally understood that a standard dose of ferrous sulfate 325 mg (65 mg elemental iron) taken by mouth three times daily generally provides sufficient elemental iron to replace iron stores and normalize Hb and Hct. Sustained-release formulations are not recommended, as they may bypass the area in the intestine where maximal absorption occurs. Combination products with iron and vitamin C (ascorbate) or L-cysteine are reported to facilitate increased iron absorption.

An iron preparation of the invention may be provided as the active ingredient in tablets or caplets, each of which contains about 10 mg to about 600 mg iron preparation (about 1 mg to about 60 mg elemental iron), together with excipients. Optionally, an iron preparation of the invention may be provided as the active ingredient in tablets or caplets, each of which contains about 1 mg to 600 mg iron preparation (about 1 mg to about 60 mg elemental iron), L-ascorbate (or its equivalent), folate (or its equivalent), vitamin B12 (or its equivalent), and biotin, together with excipients.

It is known that overdoses of iron could be fatal. The in vitro studies disclosed herein show that an iron preparation of the invention is bioavailable and useful for replacing iron stores and normalizing Hb and Hct when administered by mouth. Further, the in vitro studies disclosed herein show that an iron preparation of the invention affords the advantages to the subject that lower doses of an iron preparation of the invention provide sufficient iron for physiological iron repletion as compared to the doses of conventional iron compositions that are required for physiological iron repletion. Therefore, the inventor believes that a subject ingesting an iron preparation of the invention will experience fewer side effects and a reduced risk of iron overdose and the toxicities related thereto.

In general, the pharmaceutical compositions of this invention can be prepared by conventional techniques, as are described in *Remington's Pharmaceutical Sciences*, a standard reference in this field [Gennaro A R, Ed. *Remington: The Science and Practice of Pharmacy*. 20$^{th}$ Edition. Baltimore: Lippincott, Williams & Williams, 2000]. For therapeutic purposes, the active components of this invention are ordinarily combined with one or more excipients appropriate to the indicated route of administration.

Diagnostic, Chemical, and Biological Applications of an Iron Preparation of the Invention. An iron preparation of the invention provides ferric iron for diagnostic, chemical, and biological processes that require iron. By way of example, an iron preparation of the invention may be substituted for a conventional iron salt in nutrient compositions that are used to promote the growth and/or differentiation of micro-organisms useful for applications such as converting animal wastes into useful materials (as disclosed, for example, in U.S. Pat. Nos. 3,973,043 and 5,902,742). Likewise, an iron preparation of the invention may be substituted for a conventional iron salt in nutrient compositions that are fertilizers for foliar treatment of iron-deficient plants (e.g., as in U.S. Pat. No. 5,019,149). By way of further example, an iron preparation of the invention may be substituted for a conventional iron salt in catalysts that are useful for reducing nitrogen oxides (e.g., as in U.S. Pat. No. 3,979,337), for manufacturing organic compounds or polymers (e.g., as in U.S. Pat. No. 4,900,864), for the degradation of pesticides or peroxides (e.g., as in U.S. Pat. No. 5,232,484), or for enhancing the toxicity of ingestible mollusk poisons (e.g., as in U.S. Pat. No. 5,437,870).

The following examples present useful compositions of the present invention and their anticipated outcomes in treating iron deficits in subjects requiring such treatment. The examples are representative of the scope of the invention, and as such are not to be considered or construed as limiting the invention recited in the appended claims.

EXAMPLE 1

Analysis of Samples

The tests and assays listed in Table 1 were used to characterize an iron preparation of the present invention.

TABLE 1

Tests and assays

| Test | Method | Specification |
| --- | --- | --- |
| Appearance | Visual | Yellow-green solid |
| Solubility | Dissolution | 1 gram dissolves slowly but completely in 10 cc of water |
| Identification | USP Method for Fe | Responds to the test for ferric iron |
| Identification | USP Method for Phosphorus | Responds to the test for phosphorus (as phosphate) |
| Loss on Drying | USP Method | Dry at 105° C. and report the loss in mass that is observed |
| Iron Assay | Titration | 9%-14% iron, w/w |
| pH of a 5% Solution | USP Method for pH | 2-3 |
| Phosphate Assay | Ion-Exchange | 0-3%, w/w |
| Citrate Assay | HPLC with conductivity detection | 30-60%, w/w |
| Pyrophosphate Assay | | 5-20%, w/w |
| Sodium Assay | Sodium ion electrode | 1%-15%, w/w |

EXAMPLE 2

Preparation of Unpolymerized Ferric Citrate Complexes

Experiment A. Molar ratio of $Fe^{2+}$:pyrophosphate=2:1. 2.65 g of ferrous citrate dibasic (21.1% iron by weight, Jost Chemical Co., mass equivalent to 0.01 mole of ferrous iron) was suspended in 10 mL of deionized water and 1.11 g of disodium dihydrogen pyrophosphate (0.005 mol) was added in one portion. (Disodium dihydrogen pyrophosphate is soluble in water and may be added in aqueous solution to ensure complete transfer.) After the addition, the slurry was a very pale green in color, similar to the color of the ferrous citrate dibasic. The reaction mixture was exposed to air during stirring but the reaction vessel was covered to prevent exposure of the reaction mixture to light. Over a period of several hours, the color of the slurry changed from very pale green to a grey-green but complete dissolution was not observed. After 6 days of stirring, however, all reagents dissolved and a dark green solution was obtained. The solution was filtered to remove insoluble materials; no insoluble residue was observed on the filter paper. The filtrate was concentrated to dryness to provide a yellow-green solid labeled "Product 2-1" having the properties listed in Table 2.

Experiment B. Molar ratio of $Fe^{2+}$:pyrophosphate=4:1. 2.65 g of ferrous citrate dibasic (21.1% iron by weight, Jost Chemical Co., mass equivalent to 0.01 mole of ferrous iron) was suspended in 10 mL of deionized water and 0.555 g of disodium dihydrogen pyrophosphate (0.0025 mol) was added in one portion. (Disodium dihydrogen pyrophosphate is soluble in water and may be added in aqueous solution to ensure complete transfer.) After the addition, the slurry was a very pale green in color, similar to the color of the ferrous citrate dibasic. The reaction mixture was exposed to air during stirring but the reaction vessel was covered to prevent exposure of the reaction mixture to light. Over a period of several hours, the color of the slurry changed from very pale green to a grey-green but complete dissolution was not observed. After 4 days of stirring, however, all reagents dissolved and a dark green solution was obtained. The solution was filtered to remove insoluble materials; no insoluble residue was observed on the filter paper. The filtrate was concentrated to dryness to provide a yellow-green solid labeled "Product 4-1" having the properties listed in Table 2.

Experiment C. Molar ratio of $Fe^{2+}$:pyrophosphate=3:1. 2.65 g of ferrous citrate dibasic (21.1% iron by weight, Jost Chemical Co., mass equivalent to 0.01 mole of ferrous iron) was suspended in 10 mL of deionized water and 0.734 g of disodium dihydrogen pyrophosphate (0.0033 mol) was added in one portion. (Disodium dihydrogen pyrophosphate is soluble in water and may be added in aqueous solution to ensure complete transfer.) After the addition, the slurry was a very pale green in color, similar to the color of the ferrous citrate dibasic. The reaction mixture was exposed to air during stirring but the reaction vessel was covered to prevent exposure of the reaction mixture to light. Over a period of several hours, the color of the slurry changed from very pale green to a grey-green but complete dissolution was not observed. After 8 days of stirring, however, all reagents dissolved and a dark green solution was obtained. The solution was filtered to remove insoluble materials; no insoluble residue was observed on the filter paper. The filtrate was concentrated to dryness to provide a yellow-green solid labeled "Product 3-1" having the properties listed in Table 2.

Experiment D. Molar ratio of $Fe^{2+}$:pyrophosphate=5:1. 2.65 g of ferrous citrate dibasic (21.1% iron by weight, Jost Chemical Co., mass equivalent to 0.01 mole of ferrous iron) was suspended in 10 mL of deionized water and 0.444 g of disodium dihydrogen pyrophosphate (0.002 mol) was added in one portion. (Disodium dihydrogen pyrophosphate is soluble in water and may be added in aqueous solution to ensure complete transfer.) After the addition, the slurry was a very pale green in color, similar to the color of the ferrous citrate dibasic. The reaction mixture was exposed to air during stirring but the reaction vessel was covered to prevent exposure of the reaction mixture to light. Over a period of several hours, the color of the slurry changed from very pale green to a grey-green but complete dissolution was not observed. After 3 days of stirring, however, all reagents dissolved and a dark green solution was obtained. The solution was filtered to remove insoluble materials; no insoluble residue was observed on the filter paper. The filtrate was concentrated to dryness to provide a yellow-green solid labeled "Product 5-1" having the properties listed in Table 2.

EXAMPLE 3

Iron Preparation Having pH Adjustment 2.65 g of ferrous citrate dibasic (21.1% iron by weight, Jost Chemical Co., mass equivalent to 0.01 mole of ferrous iron) was suspended in 10 mL of deionized water and 1.11 g of disodium dihydrogen pyrophosphate (0.005 mol) was added in one portion. (Disodium dihydrogen pyrophosphate is soluble in water and may be added in aqueous solution to ensure complete transfer.) After the addition, the slurry was a very pale green in color, similar to the color of the ferrous citrate dibasic. The reaction mixture was exposed to air during stirring but the reaction vessel was covered to prevent exposure of the reaction mixture to light. Over a period of several hours, the color of the slurry changed from very pale green to a grey-green but complete dissolution was not observed. After 9 days of stirring, however, all reagents dissolved and a dark green solution was obtained. The solution was filtered to remove insoluble materials; no insoluble residue was observed on the filter paper. The pH of the solution was adjusted from an initial pH of 2.7 to a final pH of 5.0 by the dropwise addition of 1 N NaOH. During the addition, the color of the solution turned from dark green to dark green-black. No precipitate formed. The solution was filtered; no insoluble residue was observed on the filter paper. The filtrate was concentrated to dryness to provide a yellow-green solid having the properties listed in Table 3.

TABLE 3

| Test or Assay | Specification | Result |
| --- | --- | --- |
| Appearance | Yellow-green solid | Conforms |
| Water solubility | Highly soluble | Conforms |
| pH of a 5% Solution | 4-6 | 5.0 |
| Iron Assay | 9%-14%, w/w | 10.3% |
| Phosphate Assay | 0-3%, w/w | 1.1% |
| Citrate Assay | 30-60%, w/w | 37.7% |
| Pyrophosphate Assay | 5-20%, w/w | 18.7% |
| Sodium Assay | 1%-15%, w/w | 11.8% |

EXAMPLE 4

Oxidation of Ferrous Citrate Dibasic with Oxygen in the Presence of Dihydrogen Disodium Pyrophosphate 2.65 g of ferrous citrate dibasic (21.1% iron by weight, Jost Chemical Co., mass equivalent to 0.01 mole of ferrous iron)

TABLE 2

| | Product Characteristics | | | |
| --- | --- | --- | --- | --- |
| Test or Assay | Expt. A Product 2-1 | Expt. B Product 4-1 | Expt. C Product 3-1 | Expt. D Product 5-1 |
| Appearance | Yellow-green solid | Dark yellow-green solid | Light yellow-green | Dark yellow-green solid |
| Water solubility | Very soluble | Soluble | Very soluble | Soluble |
| pH of a 5% Solution | 2.7 | 2.1 | 2.3 | 2.1 |
| Iron Assay | 10.1% (w/w) | 13.3% (w/w) | 12.7% (w/w) | 12.7% (w/w) |
| Phosphate Assay | 0.6% (w/w) | 0.4% (w/w) | 0.6% (w/w) | 0.4% (w/w) |
| Citrate Assay | 33.4% (w/w) | 47.0% (w/w) | 44.9% (w/w) | 61.5% (w/w) |
| Pyrophosphate Assay | 18.5% (w/w) | 11.1% (w/w) | 11.1% (w/w) | 5.8% (w/w) |
| Sodium Assay | 4.4% (w/w) | 2.4% (w/w) | 3.3% (w/w) | 1.8% (w/w) | was suspended in 10 mL of deionized water and 1.11 g of disodium dihydrogen pyrophosphate (0.005 mol) was added in one portion. (Disodium dihydrogen pyrophosphate is soluble in water and may be added in aqueous solution to ensure complete transfer.) After the addition, the slurry was a very pale green in color, similar to the color of the ferrous citrate dibasic. The reaction mixture was stirred and oxygen gas was bubbled in; the reaction vessel was covered to prevent exposure of the reaction mixture to light. Over a period of several hours, the color of the slurry changed from very pale green to a grey-green but complete dissolution was not observed. After 14 days of stirring, the slurry remained grey-green in color and dissolution remained incomplete. It was concluded that oxidation of ferrous citrate to ferric citrate by oxygen gas occurred too rapidly; added dihydrogen pyrophosphate did not prevent polymerization of the ferric citrate that formed.

EXAMPLE 5

Oxidation of Ferrous Citrate Dibasic with Hydrogen Peroxide in the Presence of Dihydrogen Disodium Pyrophosphate 2.65 g of ferrous citrate dibasic (21.1% iron by weight, Jost Chemical Co., mass equivalent to 0.01 mole of ferrous iron) was suspended in 10 mL of deionized water and 1.11 g of disodium dihydrogen pyrophosphate (0.005 mol) was added in one portion. (Disodium dihydrogen pyrophosphate is soluble in water and may be added in aqueous solution to ensure complete transfer.) After the addition, the slurry was a very pale green in color, similar to the color of the ferrous citrate dibasic. The reaction mixture was stirred; the reaction vessel was covered to prevent exposure of the reaction mixture to light. Over a period of several hours, the color of the slurry changed from very pale green to a grey-green but complete dissolution was not observed. After 24 hours of stirring, 40% hydrogen peroxide was added dropwise. The reaction mixture became yellow-green in color but dissolution of the starting materials remained incomplete. It was concluded that oxidation of ferrous citrate to ferric citrate by hydrogen peroxide occurred too rapidly; added dihydrogen pyrophosphate did not prevent polymerization of the ferric citrate that formed.

EXAMPLE 6

Iron Uptake by Caco-2 Cells

Caco-2 cells in culture will be used to evaluate iron uptake from solutions of an iron preparation of the invention under a variety of experimental conditions, including uptake from solutions also containing substances known to enhance or inhibit iron uptake from the gastrointestinal tract (e.g., L-ascorbate and phytate, respectively).

Cell culture. Caco-2 cells are obtained from the American Type Culture Collection at passage 17 and used in experiments at passage 29-35. Cells are seeded at a density of 50,000 cells/cm$^2$ in collagen-treated 6-well or 24-well plates. The integrity of the monolayer is verified by optical microscopy. The cells are cultured at 37° C. in an incubator with a 5% $CO_2$ and 95% air atmosphere at constant humidity. The cells are maintained in Dulbecco's Modified Eagle Medium (DMEM) plus 1% antibiotic/antimycotic solution, 25 mmol/L HEPES and 10% fetal bovine serum; the medium is changed every 2 days. Two days before the experiment, the growth medium is removed from each culture well, and the cell layer is washed and maintained with Minimum Essential Media (MEM) at pH 7.0. The MEM is supplemented with 10 mmol/L PIPES, 1% antibiotic/antimycotic solution, 4 mg/L hydrocortisone, 5 mg/L insulin, 5 µg/L selenium, 34 µg/L triiodothyronine and 20 µg/L epidermal growth factor. The enriched MEM contains less than 80 µg iron/L (1.43 µmol Fe/L), which, compared with the additional 20 or 50 µmol/L iron sources added in the following studies, is insignificant. Iron uptake experiments are conducted 13 days post-seeding.

Protocol for direct application of samples on Caco-2 cell monolayers. Caco-2 cells are seeded and maintained as described above. Solutions of the various iron samples are mixed with MEM, and the mixtures are placed directly on the cell monolayers. The Caco-2 cells are incubated with various treatments for about 20 hours before harvesting. Cellular ferritin and total protein are then analyzed and compared among all treatments.

Experimental Results. It is expected that experimental data will indicate that the ferric iron from an iron preparation of the invention is available for uptake by the cells. Ferritin production from each test article is expected to be equivalent to about 300 ng ferritin per milligram of protein, a quantity of ferritin significantly greater than that produced after exposure to ferrous sulfate, ferrous bisglycinate, sodium iron EDTA, and conventional iron sources. L-Ascorbate and L-cysteine are expected to enhance iron uptake and ferritin production from each iron preparation of the invention. If these results are obtained, the study will verify that iron from an iron preparation of the invention is taken up and used by the cells efficiently and effectively for ferritin production. The data will support the conclusion that an iron preparation of the invention will be orally bioavailable to humans and other mammals.

EXAMPLE 7

Iron Binding to Human Apotransferrin

The following test articles were evaluated in this study: Products 2-1 through 2-4 (described in Example 2); soluble ferric pyrophosphate (SFP), lot 112362 manufactured by The Dr. Paul Lohmann Chemical Company, Emmerthal, Germany ("Lohmann"); and ferric sulfate:NTA chelate.

Experimental Details. A method described by Bates was utilized to determine the rate and extent of iron uptake from each iron chelate to the iron binding sites of human apotransferrin. A solution of human apotransferrin was prepared, and an iron source, by way of a solution of a test article, was added. The binding of iron to apotransferrin was monitored at 470 nm, the absorption maximum for ferric transferrin. Absorbance readings were taken at multiple intervals during the reaction until a defined point of saturation was reached.

To decrease sources of iron contamination, all glassware used in this experiment was acid washed, in triplicate, with 50% nitric acid (v/v), followed by a triple rinse with deionized water. Disposable cuvettes were also acid washed prior to use, and all spatulas used for sample preparation were plastic. Tris buffer, $5\times10^{-3}$ M, containing $5\times10^{-2}$ M bicarbonate was used as diluent for all sample and protein solutions. Bicarbonate ion was present in the buffer in excess to ensure sufficient concentration for the formation of ferric transferrin. The buffer was adjusted to a final pH of 7.5 with dilute hydrochloric acid prior to use.

Human apotransferrin was prepared at a target concentration of $1\times10^{-4}$ M in Tris buffer, pH 7.5. As the protein contains two separate and independent metal binding sites, test samples were prepared at an iron concentration of $2\times10^{-4}$ M in Tris buffer, pH 7.5. Nitrilotriacetic acid (NTA) was utilized as a control chelating agent. A solution containing $2\times10^{-4}$ M of NTA and ferric sulfate at a target iron concentration of $2\times10^{-4}$ M was prepared in Tris buffer, pH 7.5. The NTA-Iron chelate exists as a monomeric molecular species, has been reported to react with apotransferrin immediately, and was used as a control solution for comparison with the test article preparations. A blank reaction using TRIS buffer instead of a test or control sample was also performed to determine the amount, if any, of interfering iron from the diluent.

The reaction was monitored by ultraviolet (UV) absorbance at 470 nm, the absorbance maximum for ferric transferrin. The temperature of the UV chamber was thermostatted to 25.0° C. during analysis using a recirculating water bath. For each blank, control, and sample analysis, an acid-rinsed cuvette was placed into the UV cell to which 700 µL of sample solution was added. 700 µL of the apotransferrin solution was then added to the sample, and scanning was started immediately. The spectrometer was equipped with an electronic data control program which recorded an absorbance reading at 470 nm every 10 seconds for the duration of the experiment. The experiment was discontinued at a point where the absorbance stopped rising by visual observation.

Results. Experimental data are graphically displayed in FIG. 1. The data show that iron from an iron preparation of the invention is taken up by human apotransferrin more rapidly than iron from soluble ferric pyrophosphate (SFP; Paul Lohmann GmbH, lot 112362) or ferric sulfate:NTA chelate. The data also show that an iron preparation of the invention provides iron as effectively as ferric sulfate:NTA chelate, an iron source that is known to load human apotransferrin with near quantitative efficiency.

EXAMPLE 8

Clinical Study of the Safety and Efficacy of an Iron Complex Composition of the Invention Study Design: The study will be a randomized, blinded, dose-ranging study of the safety and efficacy of an oral iron supplement comprising an iron composition of the invention in male and female blood donors who are deferred due to hemoglobin (Hgb) less than 12.5 g/dL. The study will be conducted at a blood donation center (blood bank).

Study Objectives: The PRIMARY OBJECTIVE of the study is to test the safety of giving daily doses of 20- or 40-mg oral iron as a stable, unpolymerized ferric citrate chelate composition of the invention to male and female blood donors who had Hgb<12.5 g/dl. The SECONDARY OBJECTIVE of the study is efficacy, which will be assessed as improvement in symptoms of iron depletion/deficiency and normalization of laboratory values for hemoglobin, hematocrit, serum ferritin, and soluble transferrin receptor levels. In addition, a standardized assessment of subjective response to iron therapy will be completed using a standardized questionnaire. The objective of this assessment will be to test the hypothesis that iron supplementation has positive effects on subjective symptoms of constipation, abdominal cramping, diarrhea, nausea/vomiting, metallic taste in the mouth, and other symptoms known to be related to oral iron supplementation with conventional iron supplements.

We will assess changes in hemoglobin, serum ferritin, and soluble transferrin receptor levels in each participant at 1- and 2-month intervals post-donation or post-deferral for low hematocrit. We will assess subjective response to iron therapy using a standardized questionnaire.

Ethical Aspects: The study will be conducted as an Institutional Review Board-approved protocol. The main risk for participants is side effects related to the study medication. Based on historical data for iron fortificants, an intolerance rate of 1 per 9 individuals is expected. Volunteers will give informed consent prior to participation in the study.

Study Participants: About 250 study participants will be recruited among individuals coming spontaneously to the center to donate blood. All donors meeting AABB, FDA, and local blood center donor eligibility criteria but are deferred for a fingerstick hemoglobin value of less than 12.5 mg/dL who give informed consent to participate in the trial will constitute the "test group." Exclusion criteria in both groups include ages less than 18, psychiatric conditions or diseases that render the participant unable to give informed consent, or a prior diagnosis of hemochromatosis. In addition, donors will be excluded if they are taking iron supplements or multiple vitamins and don't know if it contains iron.

All participants will give informed consent. They will than undergo health history screening and record review to determine blood donation frequency, history of low fingerstick hemoglobin values, current or past iron therapy, history of gastrointestinal or genitourinary blood loss, obstetric and gynecologic history, medications, diet, and personal or family history of anemia, clotting or bleed disorders, hemochromatosis, hemoglobinopathy, or cancer. The presence of pica (persistent craving and compulsive consumption of non-nutritive substances) will be specifically assessed.

A physician working at the blood center will be responsible for seeing all potential participants. Once eligibility criteria for a blood donation have been fulfilled, a fingerstick hemoglobin value will be obtained. If the hemoglobin value is less than 12.5 g/dL, the individual will be informed of the test result and asked to participate in the study.

Treatment: Subjects in the test group will receive 120 tablets (a 60-day supply) of the test article (tablets of stable, water-soluble, unpolymerized ferric citrate chelate composition of the invention containing 0, 20, or 40 mg of elemental iron) at the time of their deferral or post-donation. Subjects in the control group will receive 120 tablets (a 60-day supply) of the control article (tablets of ferrous gluconate containing 20 mg of elemental iron). Tablets will be dispensed in child-resistant blister packs. Subjects will be instructed to take two tablets by mouth daily, 30 minutes before bedtime, with a half glass of water. Subjects will be instructed to notify a study physician promptly if adverse effects occur. Donors who develop intolerance to the tablets during the study will be given ferrous gluconate 325 mg tablets (38 mg of elemental iron).

Within 10 days of the initial visit, a study physician will inform donors of their laboratory results and inquire about compliance with and tolerance to iron therapy. Control donors found to have iron deficiency (ferritin values below the normal range of 9 mcg/L in females and 18 mcg/L in males) will be offered iron replacement tablets at the time they are notified of their laboratory results. Donors whose responses to health history screening questions and/or whose laboratory results indicate a potentially serious health concern will be referred to their primary care physician for follow-up.

Laboratory Testing: Testing will be completed at the time of enrollment in the study, and 30±5 and 60±5 days after enrollment. Capillary fingerstick hemoglobin values will be obtained using a portable hemoglobin screening device. Samples for complete blood counts (CBC) will be collected by venipuncture and analyzed by an automated hematology instrument. Serum iron determinations will be performed on an automated chemistry analyzer. Serum ferritin and transferrin levels will be determined using an automated chemistry analyzer.

Statistical Methods: Analyses will be stratified by gender among the test and control groups. In addition, in order to demonstrate the safety of iron replacement therapy in donors with low fingerstick hemoglobin values and ferritin values not indicative of iron depletion/deficiency, the low hemoglobin group will be further stratified by initial ferritin levels as "iron deficient" (ferritin below the normal range of 9 mcg/L in females and 18 mcg/L in males) or "iron depleted" (ferritin of 9-19 mcg/L in females and 18-29 mcg/L in males). Group outcomes will be compared using Student's t-test and proportions among groups compared using a Chi-square analysis for two by two contingency tables. When appropriate, paired t-tests will be used, with statistical significance defined as $p<0.05$.

Expected Results. Given the results of in vitro studies, it is reasonable to expect that clinical data will confirm that iron from an iron preparation of the invention is orally bioavailable to the subjects. Further, it is expected that the clinical data will confirm that lower doses of an iron preparation of the invention are sufficient for iron repletion as compared to the doses of conventional iron sources. It is also expected that the subjects will report fewer side effects after ingesting an iron preparation of the invention as compared to the number of side effects experienced after ingestion of a conventional iron source. If these results are obtained, they will verify that an iron preparation of the invention is both bioavailable and safe for humans.

All mentioned references are incorporated by reference as if here written. When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

Without further elaboration, it is believed that one skilled in the art can, using the preceding description, utilize the present invention to its fullest extent. The specific embodiments are, therefore, to be construed as merely illustrative, and not limitative of the remainder of the disclosure in any way whatsoever.

We claim:

1. A stable, water-soluble, unpolymerized ferric citrate chelate composition, having, by weight, from about 9% to about 14% iron, from about 30% to about 60% citrate, from about 5% to about 20% pyrophosphate, and from about 1% to about 15% sodium, wherein said composition is essentially free of sulfate.

2. The composition of claim 1, wherein said composition has a molar ratio of $Fe^{3+}$ to pyrophosphate of from about 2:1 to 5:1 and a citrate:pyrophosphate ratio of from about 2:1 to 5:1.

3. The composition of claim 1, wherein said composition has a molar ratio of $Fe^{3+}$ to pyrophosphate of from about 1.8:1 to 2.2:1 and a citrate:pyrophosphate ratio of from about 1.8:1 to 2.2:1.

4. The composition of claim 2, wherein 1 gram of said composition dissolves essentially to completion in 10 ml of water in about 15 minutes.

5. The composition of claim 2, wherein 1 gram of said composition dissolves essentially to completion in 10 ml water after adjustment of pH to about 5.

6. The composition of claim 1, wherein an aqueous solution containing 5 weight percent of said composition has a pH of from about 2 to 3.

7. The composition of claim 1, wherein said composition is essentially free of ammonia.

8. A method of preparing a stable, water-soluble, unpolymerized ferric citrate chelate composition comprising combining ferrous citrate dibasic and disodium dihydrogen pyrophosphate in water, exposing the resulting mixture to oxygen in a volume sufficient to oxidize the ferrous iron to ferric iron and at a rate sufficiently slow to allow complex formation between iron(III), citrate, and pyrophosphate as oxidation occurs, and isolating a stable, unpolymerized iron(III) citrate complex by removing water therefrom.

9. The method of claim 8 wherein oxygen is added as a gas containing from about 5% to about 25% oxygen.

10. A method of administering iron to a subject in need of such administration for the prevention or treatment of iron-deficiency or anemia comprising administering a therapeutic quantity of a stable, water-soluble, unpolymerized ferric citrate chelate composition, having, by weight, from about 9% to about 14% iron, from about 30% to about 60% citrate, from about 5% to about 20% pyrophosphate, and from about 1% to about 15% sodium, wherein said composition is essentially free of sulfate.

11. The method of administering of claim 10 wherein said administering is oral or intravenous.

12. The method of claim 10 wherein the therapeutic quantity of a stable, water-soluble, unpolymerized ferric citrate chelate composition is administered together with therapeutic quantities of ingredients selected from the group consisting of a pharmaceutically acceptable form of L-ascorbate, a pharmaceutically acceptable form of folic acid, a pharmaceutically acceptable form of vitamin B12, and a pharmaceutically acceptable form of biotin.

13. A method of administering iron to a chemical or biological system having a deficiency in iron comprising administering a quantity of a stable, water-soluble, unpolymerized ferric citrate chelate composition sufficient to correct the deficiency in iron in the system, wherein said composition has, by weight, from about 9% to about 14% iron, from about 30% to about 60% citrate, from about 5% to about 20% pyrophosphate, and from about 1% to about 15% sodium, wherein said composition is essentially free of sulfate.

* * * * *